United States Patent [19]

Fennimore et al.

[11] 4,427,003

[45] Jan. 24, 1984

[54] BANDAGES

[75] Inventors: Jack Fennimore, Welwyn; William D. Potter, Bishops Stortford; Sinan B. Kiamil, Harlow, all of England

[73] Assignee: Smith & Nephew Associated Companies Ltd., London, England

[21] Appl. No.: 342,519

[22] Filed: Jan. 25, 1982

[30] Foreign Application Priority Data

Feb. 9, 1981 [GB] United Kingdom ............... 8103916

[51] Int. Cl.³ ............................................. A61L 15/07
[52] U.S. Cl. .................................... 128/90; 427/341; 428/253; 428/272; 428/273; 428/423.5; 428/423.7; 428/424.8; 428/425.6
[58] Field of Search ................. 128/90; 428/253, 272, 428/273, 423.5, 423.7, 424.8, 425.6; 427/341

[56] References Cited

U.S. PATENT DOCUMENTS

| | | | |
|---|---|---|---|
| 3,108,975 | 10/1963 | Lambert et al. | |
| 3,373,741 | 3/1968 | Hill et al. | |
| 3,375,822 | 4/1968 | Rose | 128/90 |
| 3,643,656 | 2/1972 | Young | 128/90 |
| 3,656,475 | 4/1972 | Hanrahan | 128/90 |
| 3,943,075 | 3/1976 | Fishbein et al. | |
| 4,020,832 | 5/1977 | Kirkpatrick et al. | |
| 4,105,025 | 8/1978 | Wang et al. | 128/90 |
| 4,131,114 | 12/1978 | Kirkpatrick et al. | 128/90 |
| 4,309,990 | 1/1982 | Brooks et al. | 128/90 |
| 4,316,457 | 2/1982 | Liegeois | 128/90 |

FOREIGN PATENT DOCUMENTS

| | | |
|---|---|---|
| 6094 | 1/1980 | European Pat. Off. . |
| 2353212 | 4/1975 | Fed. Rep. of Germany . |
| WO81/00671 | 3/1981 | PCT INT'L Appl. . |
| 1578895 | 11/1980 | United Kingdom . |

*Primary Examiner*—James C. Cannon
*Attorney, Agent, or Firm*—Jacobs & Jacobs

[57] ABSTRACT

Water hardenable splinting bandages comprising a flexible fabric carrying an isocyanate terminated prepolymer having a reaction functionality of not less than two and a catalyst which bandage is characterized in that the prepolymer is a water absorbing isocyanate terminated prepolymer and the catalyst is water soluble but insoluble in the prepolymer, compositions therefore and processes of manufacture thereof are described.

11 Claims, No Drawings ized a 4,427,003

BANDAGES

The present invention relates to water hardenable polyurethane orthopaedic splinting bandages and their manufacture and to materials for use therein.

Recently attempts have been made to make water hardenable bandages from plastics such as polyurethane. British Patent Specification No. 1,578,895 discloses a water hardenable bandage material of an air permeable flexible fabric impregnated and/or coated with an isocyanate terminated prepolymer which is a reaction product of an aromatic isocyanate and a polyol containing a tertiary amino nitrogen, for example propoxylated triethanolamine. These bandages however are believed to have a somewhat short shelf life. It would be desireable to produce a polyurethane based bandage which has good storage properties. Such bandages have now been discovered.

The present invention provides a water hardenable splinting bandage comprising a flexible fabric carrying an isocyanate terminated prepolymer having a reaction functionality of not less than two and a catalyst which bandage is characterised in that the prepolymer is a water absorbing isocyanate terminated prepolymer and the catalyst is water soluble but insoluble in the prepolymer.

In apt bandages of the invention the reaction functionality of isocyanate terminated prepolymer is two.

In favoured bandages of the invention the reaction functionality of the isocyanate terminated prepolymer is more than two.

In apt isocyanate terminated prepolymers the isocyanate is an aromatic isocyanate. In favoured isocyanate terminated prepolymers the isocyanate is an aliphatic isocyanate which results in even better storage stability than occurs with aromatic isocyanates.

In a favoured aspect the present invention provides a water hardenable splinting bandage comprising of a flexible fabric carrying an isocyanate terminated prepolymer having a reaction function ability of more than two and a catalyst which bandage is characterised in that the prepolymer is a water absorbing aliphatic isocyanate terminated prepolymer and the catalyst is water soluble but insoluble in the prepolymer.

The catalyst is capable of promoting a rapid reaction of the isocyanate terminated prepolymer such as an aliphatic isocyanate terminated prepolymer with the water but in the absence of water is inert. The catalyst is insoluble in the isocyanate terminated prepolymer in the absence of water but is soluble in the prepolymer phase in the presence of water.

Aptly the catalyst is an inorganic material which has an alkaline reaction in water. Most aptly the catalyst is a carbonate or bicarbonate.

Suitable solid, water soluble carbonate or bicarbonate catalysts include topically acceptable alkali metal carbonates and bicarbonates. Favoured catalysts of this kind are sodium carbonate and potassium carbonate of which potassium carbonate is preferred.

The catalyst present in the bandage will normally be from 0.1% to 40% by weight, preferably 2% to 20% by weight and desirably 3% to 10% by weight of the prepolymer, for example 4, 5 or 6%.

The catalyst is normally and preferably present in admixture with the prepolymer.

The catalyst is preferably present in the mixture as a finely divided solid. Most aptly the maximum particle size of the catalyst is below 150$\mu$ and favourable below 56$\mu$. The average particle size of the catalyst is generally below 75$\mu$ and is preferably from 30 to 40$\mu$.

The isocyanate terminated prepolymer for example an aliphatic isocyanate terminated prepolymer of the splinting bandage of the invention must be capable of rapidly reacting with water in the presence of the catalyst to form a rigid cast. These prepolymers can have a reaction functionality of two.

Favoured prepolymers have a reaction functionality of greater than two. A three dimensional cross-linked structure will be formed when such prepolymers are reacted with water. Preferred isocyanate terminated polyether prepolymers have a reaction functionality of 2 to 3. Generally the functionality of the prepolymer is not greater than 9 and usually not greater than 6.

The isocyanate terminated prepolymer is preferably in a fluid form ranging from a liquid to a semi solid in the bandage so that during setting adjacent layers of the bandage in the cast will adhere and bond together. The isocyanate terminated prepolymer absorbs water so that rapid setting takes place.

Suitable prepolymers are derived from an ethylene oxide adduct which has a reaction functionality of two or more than two and an isocyanate which has a reaction functionality of two or more than two. The reaction functionality of the isocyanate is preferably two.

The ethylene oxide adduct employed can be an ethylene oxide polymer with a functionality of two.

The ethylene oxide adduct may be derived from ethylene oxide and a polyol or polyamine with a functionality of two or more than two, for example a hydroxyl functionality three to six or an amino functionality of two. The ethylene oxide may be prepolymerised.

Preferably a polyol (rather than a polyamine) is employed. Aptly the polyol is a diol or triol.

The uncapped prepolymer will preferably contain sufficient oxyethylene units to render the prepolymer water absorbent.

Suitable ethylene oxide adducts include homopolymers of ethylene oxide and copolymers of ethylene oxide with propylene oxide or tetramethylene oxide containing at least 30% by weight or ethylene oxide residues. Other suitable ethylene adducts include polyester capped with ethylene oxide residues.

Suitable ethylene oxide adducts are polyethylene glycols. Favoured polyethylene glycols have been found to have a molecular weight of 100 to 3000, more suitably 200 to 2000 and preferably 500 to 1500.

Suitable polyols include glycerol, triethanolamine, and pentaerythritol, 1,1,1-trimethylolpropane, sorbitan and its monoalkylesters, castor oil and hydrogenated castor oil. Suitable polyamines include ethylene diamine and 1,3-diaminopropane.

Favoured ethylene oxide adducts include polyoxyethylene sorbitan esters, ethoxylated castor oil, ethoxylated hydrogenated castor oil and ethylene oxide adducts of glycerol.

Preferred ethylene oxide adducts are polyoxyethylated sorbitan esters such as the surfactant known as Tween 20 marketed by Honeywell Atlas Ltd. Tween 20 is a polyoxyethylene sorbitan monolaurate with a hydroxyl functionality of three.

Other preferred polyethers are ethoxylated castor oils such as Etocas 10 and Etocas 35 marketed by Croda Chemicals Ltd. Etocas 10 is castor oil with 10 moles of ethylene oxide added. Etocas 35 is a castor oil with 35 moles of ethylene oxide added. Both Etocas 10 and Etocas 35 have a hydroxyl functionality of three.

Yet other preferred polyethers are ethoxylated hydrogenated castor oils such as Croduret 10 and Croduret 30 marketed by Croda Chemicals Limited. Croduret 10 is a hydrogenated castor oil with 10 moles of ethylene oxide added. Croduret 30 is a hydrogenated castor oil with 30 moles of ethylene oxide added. Both Croduret 10 and Croduret 30 have hydroxyl functionality of three.

Preferred ethylene oxide adducts of glycerol are these containing 12 to 36 moles of ethylene oxide per mole of glycerol, for example glycerol ethoxylated with 18 moles of ethylene oxide.

Another preferred ethylene oxide adduct of glycerol is known by the code reference 15-200 made by Dow Chemicals. 15-200 is an oxypropylated ethylene oxide adduct of glycerol of molecular weight 2160. A further preferred ethylene oxide adduct of glycerol is an ethoxylated glycerol of molecular weight of between 1200 and 1300.

The isocyanates for reacting with the ethylene oxide adduct to form the isocyanate terminated polyether include the aliphatic (including alicyclic) isocyanates and aromatic isocyanates.

The use of aliphatic isocyanates has special advantages in that it has been found that the resultant polymers are more stable in the absence of water, have better light stability and are less coloured than prepolymers made with aromatic isocyanates.

A favoured aliphatic isocyanate is methylene-bis-(4-cyclohexylisocyanate) known as Hylene W marketed by Dupont and Desmodur W marketed by Bayer. Another favoured aliphatic isocyanate is N,N'-bis(6-isocyanatohexyl) urea known as Desmodur N marketed by Bayer. Yet another favoured aliphatic isocyanate is N,N' 2-tris (6-isocyanatohexyl) imidodicarbonicdiamide known as Desmodur N75 marketed by Bayer.

The aromatic polyisocyanates can be any of the aromatic polyisocyanates general known in polyurethane chemistry for example as described in 'Polyurethanes Chemistry and Technology Part I' Interscience Publishers (1962). A favoured aromatic polyisocyanates is 4,4'-diphenylmethane diisocyanate known as Desmodur M44 marketed by Bayer.

The polyisocyanates may be modified before use. The polyisocyanate may be pre-reacted with water generally present in a polyethylene glycol or a polyol such as glycerol.

Favoured isocyanate terminated prepolymers have hard blocks incorporated in their polymer chains. The presence of such hard blocks in the prepolymer will substantially increase the stiffness of a set cast made from the prepolymer.

Suitable hard blocks contain urea groups or urethane groups. Preferred isocyanate terminated prepolymers of the invention have hard block containing urea groups.

Such hard blocks are usually hydrophobic in character. Desirably the proportion of hard blocks in the prepolymer is chosen so as to maximise the stiffness in the set cast formed from the prepolymer without destroying the water absorbing properties of the prepolymer.

The bandages of the invention consist of flexible fabric carrying the prepolymer. The flexible fabric carrier has apertures of sufficient size to enable water to permeate the bandage and react with the prepolymer.

Suitable aperture sizes are 2 mm to 100 mm preferably 5 mm to 50 mm. Suitable flexible fabrics can be woven, knitted or non woven fabrics made of materials which are inert to the prepolymer. Suitable materials include polyester, polyamides, polyolefine and glass fibre or mixtures thereof.

Favoured flexible fabric carriers include gauzes such as leno gauze and warp knitted polyester fabrics. A preferred warp knitted polyester fabric has between 40 to 50 apertures per square centimeter.

The amount of prepolymer on the flexible carrier should be sufficient to ensure that the resultant cast has adequate strength. Suitable amounts have been found to be 50 to 400 g/m$^2$ and preferably 100 to 200 g/m$^2$.

The bandages can be in the form of flat strips or rolls in conventional manner.

It is believed that the bandage should be protected during storage from water and moisture vapour to prevent a premature setting taking place. The bandages can be conventionally packaged in heat sealed polyethylene pouches such as metal foil polyethylene laminate pouches.

In use the bandages are brought in contact with water normally by immersion and wrapped around the injured part of the body. The setting bandage has a working time sufficient to allow the bandage to be positioned and a set time when the cast is rigid. Suitable working times are 1 minute to 6 minutes preferably 2 minutes to 4 minutes. Suitable set times are 5 minutes to 30 minutes preferably 6 minutes to 15 minutes.

In another aspect the invention provides a water hardenable composition comprising a water absorbing isocyanate terminated prepolymer and a solid water soluble catalyst insoluble in the prepolymer.

Favoured isocyanate terminated prepolymers are aliphatic isocyanate terminated prepolymers.

In a further aspect the invention provides a water hardenable composition comprising a water absorbing aliphatic isocyanate terminated prepolymer and a solid water soluble catalyst insoluble in the prepolymer. Suitable prepolymers and catalysts are described hereinbefore in relation to water hardenable splinting bandages of the invention.

The prepolymer can be prepared by several different methods. In a preferred method a polyol or polyamine is reacted with the appropriate oxide and the resulting ethylene oxide adduct is then reacted with excess polyisocyanate. The polymerisation reaction may be carried out in more than one stage using different alkylene oxides in which case the ethylene oxide polymerisation should be the last stage for example the polyol or polyamine may be propoxylated in one stage and then further ethoxylated in a second stage. In a further method the polyol and/or the preformed ethylene oxide polymer may be reacted in the presence of a polyisocyanate such as an aliphatic polyisocyanate and the resulting ethylene oxide adduct reacted with excess isocyanate to form the prepolymer. It has been found advantageous to incorporate a small amount of water at the last stage during the preparation of the isocyanate terminated prepolymer such as an aliphatic isocyanate terminated prepolymer. The reaction of the polyisocyanate with water forms hard blocks containing urea groups which give improved stiffness to the resultant cast made from the prepolymer. The use of isocyanate prepolymers with hard blocks containing urea groups is a preferred aspect of the invention.

Isocyanate terminated prepolymers containing hard blocks can also be formed by reacting a preformed ethylene oxide adduct with a molar excess of isocyanate in the presence of water, an aliphatic diol or an aliphatic diamine in which the aliphatic group contains two to four carbon atoms. Suitable aliphatic diols or diamines include ethane diol, 1,3 propane diol, 1,4 butane diol and ethylene diamine.

The presence of water or an aliphatic diamine in such a reaction will lead to the formation of hard blocks containing urea groups. Similarly the presence of an aliphatic diol will lead to the formation of hard blocks containing urethane groups.

A preferred method of forming an isocyanate terminated prepolymer containing urea hard blocks comprises reacting an ethylene oxide adduct with a molar excess of a polyisocyanate in the presence of water.

The proportion of hard blocks containing urea groups in the isocyanate terminated prepolymer depends on the amount of water and molar excess of polyisocyanate present in the reaction group.

Favoured isocyanate terminated prepolymers with hard blocks containing urea groups comprised a reaction product of 1 mole of a trifunctional polyoxyethylated sorbitan monolaurate for example dry Tween 20 with 1 to 3.0 moles of water and 4.5 to 5 moles of an aliphatic di-isocyanate for example Desmodur W.

A preferred prepolymer with apt hard blocks containing urea groups comprises a reaction product of the above reactants in the mole ratio of 1:1.90:4.91.

A further group of favoured polymers with hard blocks containing urea groups comprises a reaction product of 1 mole of an oxyethylated glycerol with a molecular weight of between 1000 to 1300, 2.5 to 3.5 moles of water and 8.5 to 10.5 moles of an aliphatic diisocyanate for example Desmodur W.

A preferred prepolymer with hard blocks containing urea groups comprises the reaction product of the above reactants in the molar ratio of 1:3.42:8.52.

Yet a further group of favoured isocyanate terminated prepolymers with hard blocks containing urea groups comprises a reaction product of 1 mole of polyethylene glycol of molecular weight 600, 1 to 2 moles of water and 4 to 5 moles of an aliphatic di-isocyanate for example Desmodur W.

A preferred prepolymer with hard blocks containing urea groups comprises a reaction of the above reactants in a molar ratio of 1:1.25:4.25.

The reaction between the ethylene oxide and the polyol can be carried out at a temperature of about 120° C. in an inert atmosphere at a pressure of 20 psi to 50 psi in the presence of a basic catalyst. Suitable basic catalysts include sodium hydroxide, potassium hydroxide and basic ion exchange resins. The reaction between the ethylene oxide adduct and the polyisocyanate can be carried out at a temperature of 50° C. to 60° C. in a dry atmosphere preferably in the presence of a catalyst such as di-N-butyl tin dilaurate. The prepolymer can be purified to remove potential toxic substances by dissolving the prepolymer in a suitable solvent for example methylene chloride and extracting with hexane. The prepolymer can also be conveniently made in a solvent for example methylene chloride.

In another aspect the invention provides a method of making water hardenable splinting bandages which comprises coating/or impregnating a flexible fabric carrier with a mixture of a water absorbing isocyanate terminated prepolymer and a solid water soluble catalyst which is insoluble in the prepolymer.

Mixtures of the prepolymer and the catalyst can be formed by conventional methods in which case the prepolymer is preferably in a liquid form which may be a solution or hot melt.

Suitable solvents for the prepolymer include methylene chloride, acetone, methyl ethylketone, dimethylformamide and the like. The preferred solvent is methylene chloride.

Preferably the catalyst is in a finely divided state for example a powder and is uniformly dispersed into the prepolymer. The catalyst may alternatively be impregnated with the flexible fabric carrier before coating with the water absorbing isocyanate terminated prepolymer.

Other inert materials may be incorporated into the prepolymer mixture. These materials include powdered fillers such as alumina, fibrous reinforcing fillers for example glass fibres and colouring agents.

An apt alumina filler is G5438 available from Ramsden Limited.

The prepolymer mixture can favourably contain materials which will 'scavenge' for water for example materials which will react or absorb water. Such materials can prevent or delay premature setting of the prepolymer composition by absorbed water in the prepolymer ingredients. Suitable materials include 4,4' diphenylmethane di-isocyanate for example Desmodur M44 marketed by Bayer and molecular sieves for example Sylosiv A3 available from W. R. Grace.

Suitable 'scavenging' materials can be present in the prepolymer mixtures in an amount of 1% to 20% by weight preferable 2% to 10% by weight of the prepolymer.

The prepolymer mixture in a fluid state is then coated onto the flexible fabric carrier.

The prepolymer mixture may be sufficiently fluid without modification to be coated onto the fabric. The prepolymer mixture can also be coated in the form of a solution, a solvent dispersion or a hot melt.

Any suitable coating means can be used to coat the flexible fabric including fixed doctor blade over flat bed or roller and roller coating systems.

It is essential that the prepolymer mixture during coating is protected from moisture vapour. Suitable coating systems will be enclosed and will be conducted in an atmosphere free from moisture vapour such as dry air, or inert gases from example carbon dioxide or nitrogen.

In a preferred continuous process the prepolymer mixture as a solution dispersion in methylene chloride is coated onto a length of flexible fabric by means of a blade over flat bed coating head and the coated fabric dried in a hot oven. It is essential that the coated fabric has apertures of sufficient size and number to allow water to permeate a bandage made of the coated fabric. The coated fabric can then be split into suitable size strips and rolled up into bandages. The bandages can then be packaged into polyethylene film pouches.

The following examples illustrate the invention.

EXAMPLE 1

Preparation of Prepolymer 0.05 moles of undried Tween 20 (containing approximately 2% water) was added to a beaker and heated to 50° C., 0.28 mls. of T12 catalyst was added with stirring followed by 0.3 moles of Hylene W also with stirring. An exothermic reaction occurred which raised the temperature of the mixture to 115° C. The reaction was complete after approximately 10 minutes. The resultant prepolymer was a viscous liquid. The prepolymer was then transferred to a sealed container and stored under nitrogen.

The prepolymer (50 g) was dissolved in methylene chloride (50 g) and washed twice by a liquid—liquid extraction method using dry hexane (75 g) to purify the prepolymer. The prepolymer was then recovered by evaporating the methylene chloride and stored in a sealed container.

EXAMPLES 2 TO 7

Water hardenable compositions were prepared by mixing in a vial with a spatula 100 parts (3 g) by weight of purified prepolymer of Example 1 with 0 (control), 1, 2.5, 5, 7.5 or 10 parts by weight of potassium carbonate (Analar grade—150 micron granules) 16.7% by weight of water was then added to each mixture and the gel and set times determined.

| Example | Parts by weight of $K_2CO_3$ | Gel time (mins) | Set time (mins) |
| --- | --- | --- | --- |
| 2 | 0 | 7.0 | 13.0 |
| 3 | 1 | 2.5 | 3.5 |
| 4 | 2.5 | 2.5 | 3.0 |
| 5 | 5 | 4.0 | 5.5 |
| 6 | 7.5 | 4.0 | 5.5 |
| 7 | 10 | 3.5 | 5.0 |

Gel time - time in minutes when mixture becomes tacky and could be removed from the vial as one lump.
Set time - time in minutes when solid left no impression when pressed with a spatula.

EXAMPLES 8 TO 13

In a similar manner to examples 2 to 7 water hardenable compositions were prepared from 100 parts (3 g) by weight of the unpurified prepolymer of Example 1 mixed with 0, 1, 2.5, 5, 7.5 and 10 parts by weight of potassium carbonate. The compositions gave the following gel and set times when mixed with 16.7% by weight of water.

| Example | Parts by weight of $K_2CO_3$ | Gel time (mins) | Set time (mins) |
| --- | --- | --- | --- |
| 8 | 0 | 17.0 | 26.0 |
| 9 | 1 | 3.0 | 5.0 |
| 10 | 2.5 | 2.0 | 3.5 |
| 11 | 5 | 2.5 | 3.5 |
| 12 | 7.5 | 2.5 | 4.0 |
| 13 | 10 | 4.0 | 6.0 |

EXAMPLE 14

Preparation of Bandage

The purified prepolymer (100 g) of Example 1 was mixed with Analar grade potassium carbonate (10 g). The prepolymer mixture was spread onto 8 cm wide 612 cotton leno gauze by a blade over flat bed coating technique as a hot melt at a temperature of approximately 60° C. in a closed area purged with carbon dioxide to obtain a dry atmosphere. The bandage strip had apertured coating weight of 62 gsm. The bandage strip was cut in 1 meter lengths and rolled up. The bandage rolls were then stored in heat sealed pouches of 62.5 micron thick low density polyethylene which had previously been purged with nitrogen.

The bandage was made into a cast by immersing the bandage roll in water and wrapping the unrolled bandage around a 2.5 cm diameter spindle. The bandage had a working time of 5 minutes and a set time of 12 minutes. The resultant cast was rubbery but became hard after 24 hours.

EXAMPLE 15

An unpurified prepolymer was prepared in the same manner as Example 1 using dried Tween 20 and mole ratio of Tween 20 to Hylene W of 1:3. The resultant prepolymer was a viscous liquid.

EXAMPLE 16

A water hardenable composition was prepared by using prepolymer (3 g) of Example 15 with Analar grade potassium carbonate (0.15 g). The prepolymer mixture was mixed with water (0.53 g) to form a hard composition with a gel time of 2.25 minutes and a set time of 3 minutes.

EXAMPLE 17

The prepolymer (3 g) of Example 15 was mixed with milled glass fibre (1.26 g) and Analar grade potassium carbonate (0.15 g). The prepolymer mixture was mixed with water (0.74 g) to form a hard composition with a gel time of 2.25 minutes and a set time of 3 minutes.

EXAMPLE 18

The prepolymer mix of Example 16 was used to prepare a 10 cm × 1 meter bandage in the same manner as Example 14. The bandage had a working time of 5 minutes and a setting time of 12 minutes.

EXAMPLE 19

The prepolymer mix (300 g) of Example 17 was used to prepare a 10 cm × 1 meter bandage in the same manner as Example 14. The bandage had a working time of 5 minutes and a setting time of 12 minutes.

EXAMPLE 20

Preparation of Prepolymer in Solvent

Undried Tween 20 (1 mole containing 1.391 moles of water), water (0.51 g moles), Desmodur W (4.910 moles) and 150 ml of dry methylene chloride were added to a 500 ml flask fitted with a reflux condenser and heated to 50° C. to 60° C. with gentle stirring.

T12 catalyst (0.008 moles) was added and the heated mixture allowed to react for 100 minutes and then for a further 30 minutes without heating.

The prepolymer solution was washed to purify the prepolymer by adding dry hexane (250 ml) to the flask, shaking, leaving the mixture to separate into two layers and decanting off the top layer. The washing procedure was carried out three times.

Dry methylene chloride (50 ml) was added to the purified prepolymer to form a clear, amber solution suitable for the preparation of bandages.

The prepolymer was obtained from solution by evaporating the solvent using a rotary evaporator.

At all stages the prepolymer was stored under nitrogen to prevent contact with atmospheric moisture.

Preparation of Water Hardenable Composition

A water hardenable composition was prepared by mixing in a vial with a spatula the purified prepolymer (3 grams = 100 parts by weight), potassium carbonate—Analar grade of particle size <75 microns (5 parts by weight) and Alumina grade G5438 (10.5 parts by weight). When mixed with water (23 parts by weight) the prepolymer mixture formed a hard composition with a gel time of 3 minutes and a setting time (determined by a setting rheometer) of 9 minutes.

Preparation of Bandage

A slurry was prepared by mixing a solution of the prepolymer (100 parts by weight) in dry methylene chloride (40 parts by weight) with potassium carbonate—Analar grade with a particle size <75 μm (5 parts by weight), Alumina—Grade G5438 (7 parts by weight), Sylosiv A3 (3 parts by weight) and Desmodur M44 (9 parts by weight).

The slurry was coated onto a 10 cm wide strip of a warp knitted polyester substrate (69 g/m$^2$), having 41 holes per cm$^2$, by means a doctor knife over flat bed coating head, set at a gap of 40 microns and the coated strip and dried at approximately 20° C. The bandage strip had an apertured coating with a weight per square meter of 150 g. The bandage strip was cut into 1 meter lengths and spooled into rolls on a cruciform core. The bandage rolls were then stored in heat sealed pouches of low density polythene (thickness 62.5 microns) which had previously been purged with nitrogen.

A bandage was made into cast by immersing a bandage roll in water and wrapping the unrolled bandage around a 2.5 cm diameter spindle. The bandage had a working time of 2.5 minutes and a set time of 10 minutes.

A 70 mm wide cylinder of the set cast gave a break load of 425 Kgf when compressed axially at 5 cm per minute in an Instron Testing Machine.

EXAMPLE 21

Preparation of an Ethoxylated Glycerol Prepolymer

A purified ethoxylated glycerol isocyanate terminated prepolymer was prepared in the same manner as the prepolymer of Example 1 using a reaction mixture of ethoxylated glycerol of molecular weight 1231 (1mole), water (3.42 moles), Desmodur W (9.84 moles) and catalyst of T12 (0.008 moles).

Preparation of Water Hardenable Composition

A water hardenable composition was prepared by mixing in a vial the purified prepolymer (3 grams≡100 parts by weight), potassium carbonate—Analar grade of particle size <75 microns (5 parts by weight) and Alumina grade G5438 (10.5 parts by weight). When mixed with water (23 parts by weight) the prepolymer mixture formed a hard composition with a gel time of 4.5 minutes and a setting time (determined by a setting time rheometer) of 10.5 minutes.

Preparation of Bandages 10 cm × 1 meter bandages were prepared in the same manner as Example 20 by coating a warp knitted polyester substrate with a slurry consisting of a mixture of the purified polymer (100 parts by weight). Potassium carbonate—Analar grade particle size <75 microns (5 parts by weight), Alumina grade G5438 (10 parts by weight) and methylene chloride (50 parts by weight) to give a dry weight per square meter of 150 g.

A bandage was made into a cast by immersing a bandage roll in water and wrapping the unrolled bandage around a 2.5 cm diameter spindle. The bandage had a working time of 4 minutes and a set time of 11 minutes.

A 70 mm wide cylinder of the set cast gave a break load of 153 Kgf when compressed axially at 5 cm per minute in an Instron Testing Machine.

EXAMPLE 22

Preparation of Polyethylene Glycol Prepolymer

A purified polyethylene glycol isocyanate terminated prepolymer was prepared in the same manner as Example 20 using a reaction mixture of polyethylene glycol of molecular weight 600 (1 mole), distilled water (1.25 mole), Desmodur W (4.25 moles) and catalyst T12 (0.008 moles).

Preparation of Water Hardenable Composition

A water hardenable composition was prepared in the same manner as Example 20 using the purified polyethylene glycol isocyanate terminated prepolymer in place of Tween 20 prepolymer in the prepolymer mixture.

When mixed with water (23 parts by weight) the prepolymer mixture formed a hard composition with a gel time of 4.5 minutes and a set time (determined by a setting time rheometer) of 10.5 minutes

What we claim is:

1. A water hardenable splinting bandage comprising a flexible fabric carrying a water absorbing isocyanate terminated prepolymer having a reaction functionality of not less than two in admixture with a solid inorganic catalyst that has an alkaline reaction with water, said inorganic catalyst being water-soluble but insoluble in the prepolymer.

2. A water hardenable splinting bandage as claimed in claim 1 in which the reaction functionality of the isocyanate terminated prepolymer is two.

3. A water hardenable splinting bandage as claimed in claim 1 in which the reaction functionality of the isocyanate terminated prepolymer is more than two.

4. A water hardenable splinting bandage as claimed in claim 2 in which the isocyanate is an aromatic isocyanate.

5. A water hardenable splinting bandage as claimed in claim 3 in which the isocyanate is an aliphatic isocyanate.

6. A water hardenable splinting bandage as claimed in claim 1 in which the catalyst comprises an alkali metal carbonate or bicarbonate.

7. A water hardenable splinting bandage as claimed in claim 1 in which the catalyst is potassium carbonate.

8. A water hardenable splinting bandage as claimed in claim 1 in which the catalyst is present in the bandage in an amount of from 2% to 20% by weight of the prepolymer.

9. A water hardenable splinting bandage of claim 1 in which the isocyanate terminated prepolymer is derived from an ethylene oxide adduct and an isocyanate.

10. A water hardenable splinting bandage as claimed in claim 1 in which the isocyanate terminated prepolymer has hard blocks containing urea groups.

11. A method of making water hardenable splinting bandages as described in claim 1 which comprises coating or impregnating a flexible fabric carrier with a mixture of said water absorbing isocyanate terminated prepolymer and said solid water soluble catalyst which is insoluble in the prepolymer.

* * * * *